United States Patent
Nord et al.

(10) Patent No.: US 10,039,936 B2
(45) Date of Patent: Aug. 7, 2018

(54) METHOD AND APPARATUS PERTAINING TO MULTI-STAGE RADIATION-TREATMENT PLAN OPTIMIZATION

(75) Inventors: Janne Nord, Espoo (FI); Yves Archambault, St-Jean-sur-Richelieu (CA)

(73) Assignee: Varian Medical Systems International AG, Cham (CH)

( * ) Notice: Subject to any disclaimer, the term of this patent is extended or adjusted under 35 U.S.C. 154(b) by 871 days.

(21) Appl. No.: 13/237,399

(22) Filed: Sep. 20, 2011

(65) Prior Publication Data

US 2013/0072742 A1    Mar. 21, 2013

(51) Int. Cl.
*A61N 5/10*    (2006.01)
(52) U.S. Cl.
CPC .................. *A61N 5/1031* (2013.01)
(58) Field of Classification Search
CPC ......... A61N 5/10; A61N 5/103; A61N 5/1031
USPC ............................................. 600/1
See application file for complete search history.

(56) References Cited

U.S. PATENT DOCUMENTS

| | | | |
|---|---|---|---|
| 7,817,778 B2 | 10/2010 | Nord et al. | |
| 2010/0054411 A1* | 3/2010 | Nord et al. | 378/65 |
| 2010/0104068 A1* | 4/2010 | Kilby et al. | 378/65 |
| 2011/0065974 A1 | 3/2011 | Rietzel | |
| 2011/0091014 A1 | 4/2011 | Siljamaki et al. | |
| 2011/0106749 A1* | 5/2011 | Krishnan et al. | 706/52 |

FOREIGN PATENT DOCUMENTS

| | | |
|---|---|---|
| EP | 2260902 A1 | 12/2010 |
| EP | 2596835 A1 | 5/2013 |

OTHER PUBLICATIONS

Choi, Richin; Authorized Officer; PCT International Search Report and Written Opinion from related International Application No. PCT/CA2012/000830 dated Jan. 23, 2013; 8 pages.
Cotrutz et al., "IMRT Dose Shaping with Regionally Variable Penalty Scheme," Medical Physics, vol. 30, No. 4, Apr. 1, 2003; Am. Assoc. Phys. Med.; pp. 544-551.
Beck, Ewa; Examiner; Extended European Search Report from related European Patent Application No. 12834356.3 dated May 6, 2015; 5 pages.

* cited by examiner

*Primary Examiner* — Thaddeus Cox
(74) *Attorney, Agent, or Firm* — Fitch, Even, Tabin & Flannery LLP

(57) ABSTRACT

A control circuit employs at least two optimization stages while developing a radiation-treatment plan. During a first optimization stage the control circuit uses a first radiation-treatment plan optimization process that employs user-selected constraints to provide general plan results. During this first optimization stage the control circuit then provides one or more opportunities for a user to modify those user-selected constraints to thereby influence the general plan results. Eventually, this first optimization stage identifies a set of resultant user-selected constraints. During the second optimization stage the control circuit then uses a second radiation-treatment plan optimization process that employs the aforementioned resultant user-selected constraints to provide an optimized radiation-treatment plan.

7 Claims, 1 Drawing Sheet

METHOD AND APPARATUS PERTAINING TO MULTI-STAGE RADIATION-TREATMENT PLAN OPTIMIZATION

TECHNICAL FIELD

This invention relates generally to radiation-treatment plans and more particular to the optimization of radiation-treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted structures and adjacent tissues, organs, or the like that are desired or even critical to continued survival of the patient. As a result, radiation is ordinarily applied in a carefully administered manner to at least attempt to restrict the radiation to a given target volume.

Many treatment plans provide for exposing the target volume to radiation from a number of different directions. Arc therapy, for example, comprises one such approach. In such a case it often becomes useful or necessary to also adjust various mechanical components (such as, for example, multi-leaf collimators) of the treatment system when moving the radiation source with respect to the target volume. A radiation-treatment plan therefore often provides information regarding useful or necessary adjustments to various mechanical components of the treatment system during such a treatment.

Such plans are often calculated using an iterative process. Beginning with some initial set of settings, a radiation-treatment planning apparatus iteratively adjusts one or more of those settings and assesses the relative worth of the adjusted plan. An iterative approach such as this is often referred to as "optimizing" the plan (where "optimizing" should not be confused with the idea of identifying an objectively "optimum" plan that is superior to all other possible plans). Optimizing such a plan can prove challenging as the overall computational requirements can be considerable. As one example in these regards, a candidate treatment plan often comprises a plurality of control points (pertaining, for example, to collimator leaf settings at each of a plurality of source angles in an arc therapy application setting).

More particularly, the radiation-treatment platform that will serve to administer the radiation treatment in accordance with the optimized plan typically has numerous corresponding physical limitations. For example, the radiation source will typically move no faster than some given speed during the treatment and the multi-leaf collimator used during that treatment can only change its aperture settings subject to some maximum speed. A treatment plan that fails to account for such physical characteristics can ultimately be unusable if the aperture settings from one position to the next are physically impossible to achieve.

In some application settings, the time required to work through such iterative calculations while accounting for the various physical limitations as pertain to the intended treatment system can result in vexing delays. These delays, in turn, can lead to expensive and undesirable equipment downtime, patient discomfort, and increased costs.

BRIEF DESCRIPTION OF THE DRAWINGS

The above needs are at least partially met through provision of the method and apparatus pertaining to multi-stage radiation-treatment plan optimization described in the following detailed description, particularly when studied in conjunction with the drawings, wherein.

Figure 1:
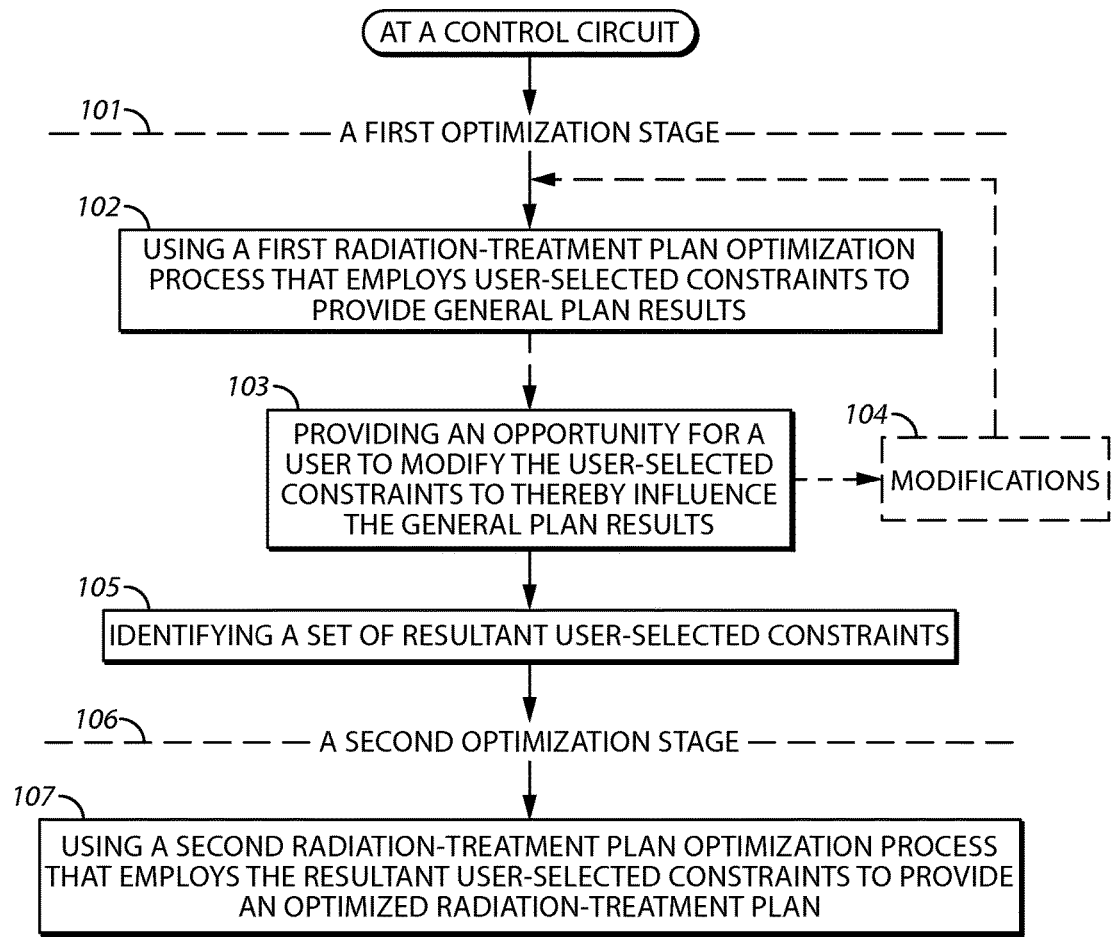
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit employs at least two optimization stages while developing a radiation-treatment plan. During a first optimization stage the control circuit uses a first radiation-treatment plan optimization process that employs user-selected constraints to provide general plan results. During this first optimization stage the control circuit then provides one or more opportunities for a user to modify those user-selected constraints to thereby influence the general plan results. Eventually, this first optimization stage identifies a set of resultant user-selected constraints. During the second optimization stage the control circuit then uses a second radiation-treatment plan optimization process that employs the aforementioned resultant user-selected constraints to provide an optimized radiation-treatment plan.

By one approach, the first radiation-treatment plan optimization process provides general plan results that are non-specific with respect to a particular radiation-delivery apparatus. The second radiation-treatment plan optimization process, however, can in fact be quite specific and precise with respect to the physical limitations or the like as pertain to a specific radiation-delivery apparatus.

That said, by one approach the first radiation-treatment plan optimization process can serve, at least in part, to model a dose-distribution shape and/or one or more dose-distribution properties as desired (although these models can be simpler as compared to models employed by the second radiation-treatment plan optimization process).

So configured, for example, the first radiation-treatment plan optimization process can essentially ignore (or generically account for) the specific parameters as pertain to a particular radiation-delivery system and instead concentrate on the generalities of the dosing regimen (such as, for example, dosing strength, angle of application, and limitation-of-exposure requirements). This, in turn, permits the first radiation-treatment plan optimization process to conclude quickly (for example, within a few seconds or even within less than one second when operating in a user-interactive phase (presuming conclusion of the requisite optimization-process initialization) using typically-available treatment-planning systems.

A user can evaluate the dosing results of the resultant plan and make changes to user-selected constraints as desired (for example, to avoid applying (or to require applying) dosages from specific angles or to permit a protected structure to nevertheless receive some amount of radiation) and then again run the radiation-treatment plan optimization process to test the effect of those modifications.

Once the first optimization stage yields generally-satisfactory results, the system can switch to the second optimization stage. A second radiation-treatment plan optimization process utilized during the second optimization stage will typically require considerably more time to yield its results (measured, sometimes, in minutes, hours, or even days). In many cases, however, this second radiation-treatment plan optimization process can be expected to conclude in a shorter period of time than might otherwise be expected because the second radiation-treatment plan optimization process can begin with the benefit of useful and vetted values for the aforementioned user-selected constraints.

Accordingly, these teachings permit a useful, machine-specific radiation-treatment plan to be optimized in a lesser period of time than might otherwise be expected. These approaches are readily enabled and can be economically fielded. These teachings are highly flexible in practice and can serve to leverage the value and utility of any number of radiation-treatment delivery systems, planning systems, or the like. These teachings are also highly scalable and can accommodate any number of machine-specific operating parameters, limitations, and constraints.

These and other benefits may become clearer upon making a thorough review and study of the following detailed description. Referring now to the drawings, and in particular to FIG. 1, an illustrative process 100 that is compatible with many of these teachings will now be presented. This illustrative example presumes that a control circuit of choice carries out the described process. Numerous possibilities exist in these regards. For example, the control circuit can comprise one or more appropriately-programmed general-purpose computers or can comprise a dedicated-purposed platform such as a radiation-treatment planning system of choice.

This process 100 includes a first optimization stage 101 and at least a second optimization stage 106. The first optimization stage 101 includes the step 102 of using a first radiation-treatment plan optimization process that employs user-selected constraints to provide general plan results. Being only "general" plan results can mean, for example, that the plan results are non-specific with respect to a particular radiation-delivery apparatus.

Accordingly, the plan results can be general in that the results do not reflect or take into account the specific limitations or abilities of a given radiation-delivery apparatus (such as, but not limited to, a particular speed by which the radiation source can move with respect to the patient, the number or type of collimators or other beam-shapers the apparatus employs, the number and/or shape of leaves that comprise any multi-leaf collimators and/or the speed at which those leaves can be moved during use, and so forth).

As a further example in these regards, it may be noted that a same machine may sometimes be used to deliver radiation in any of a variety of ways. For example, by one approach the gantry that holds the radiation source could rotate while the beam is on while pursuant to another approach this gantry could be static while the beam is on and then rotate when the beam is off. As another related example, the patient support device may move during beam on-time in one case but not move while the beam is on in another case. While these different delivery methods might be accommodate using the same machine (and hence not be characterized as a machine limitation per se), the parameters that are determined during a complete optimization process would nevertheless be different.

With the foregoing in mind, the present teachings will also permit obtaining planning results during the first optimization stage 101 that are general in that the results are independent of the delivery method. As yet further examples in these regards, the first optimization stage 101 plan results can be general in that the results are independent of the specific trajectory of the radiation beam (and hence independent of whether the trajectory is helical, a single rotation, multiple rotations, static, and so forth), whether the patient support device can move (and if so, how), whether one or more collimators can be rotated, whether the apparatus has an ability to vary the dose rate, and so forth.

Although "general" in the sense of being, for example, agnostic with respect to the operating parameters for a specific radiation-delivery apparatus, this first radiation-treatment plan optimization process can nevertheless model one or more dose-distribution shape and/or dose-distribution properties of choice in a general way. These models will typically be simpler models as pertain to the treatment target area as compared to models employed during the second optimization stage 106. For example, such a model can provide for a dose distribution having a specific distribution frequency (where, for example, a third administered dose has fewer high-frequency components than previously-administered doses). As another example, such a model can preclude dose-region isolation (by, for example, presuming that all dose photons that enter a given position also exit that position). (In practice, of course, each dose point in a target will typically have a fall-off distribution regardless of the dose-delivery methodology; when a dose level falls off quickly in one direction due to, for example, the influence of a critical organ, the dose will have a slower fall-off in some other direction.)

The user-selected constraints can pertain, for example, to non-machine-specific constraints. Examples include a general dosing specification (such as a minimum or maximum quantity of grays to be administered to the treatment target and/or surrounding tissues or structures), specific regions to avoid irradiating, specific regions to avoid as a beam-entry point, a minimum or maximum limit on the total radiation to be produced (i.e., the so-called monitor units), and so forth. These teachings will also accommodate user-selected constraints that represent biological objectives (for example, as gEUD's (generalized equivalent uniform doses) where modeled biological effects of radiation exposure are converted to one or more numerical values that can be used in an optimization process).

By one approach this step 102 can include initially presenting default values for one or more of these user-selected constraints though these teachings will also accommodate requiring the user to initially enter one or more of these values.

At step 103 this process 100 then provides an opportunity for a user to modify the user-selected constraints to thereby influence the general plan results. Operationally, this can mean running the first radiation-treatment plan optimization process and providing the results of that plan to the user via an appropriate display, printout, or the like. To the extent those general plan results are unsatisfactory in some regard the user then modifies (as denoted by reference numeral 104) one or more of the aforementioned user-selected constraints. This first optimization stage 101 then re-runs the first radiation-treatment plan optimization process to provide a new general plan result.

The user can repeat the foregoing steps as often as they wish to obtain a desired result. As the simplified first radiation-treatment plan optimization process can often be completed in less than a second with each iteration, this entire first optimization stage 101 can be completed in a short period of time. (These teachings will accommodate, if desired, permitting the user to identify some desired plan result and to configure step 103 to provide automated incremental adjustments to the user-selected constraints until the desired plan result is attained.)

When the first optimization stage 101 attains desired general plan results, step 105 identifies the set of resultant user-selected constraints that permitted this result.

By way of illustration, the user may seek to develop a radiation-treatment plan for a small tumor located adjacent the patient's spine. The user may initially identify the patient's spine as being a region that shall receive zero grays. The first radiation-treatment plan optimization process, however, may quickly reveal that this user-selected constraint, appropriate as it might be as a general proposition, renders it impossible to sufficiently irradiate the tumor to achieve the necessary therapeutic result more-or-less regardless of the radiation-delivery apparatus that one might employ. This first optimization stage 101 permits the user to incrementally relax that constraint regarding irradiation of the spine until it becomes generally possible to likely succeed with the primary task of treating the tumor.

During the second optimization stage 106 the control circuit, at step 107, uses a second radiation-treatment plan optimization process that employs the aforementioned resultant user-selected constraints to provide an optimized treatment plan. This second radiation-treatment plan optimization process comprises a more precise optimization process than the first radiation-treatment plan optimization process.

This can comprise, for example, a higher-resolution version of the first radiation-treatment plan optimization process. This can also comprise using a completely different optimization approach as compared to the first radiation-treatment plan optimization process. Numerous radiation-treatment plan optimization processes are known in the art and will suffice in these regards. As these teachings are not particularly sensitive to any particular choices in these regards, further elaboration here regarding high-resolution machine-specific optimization methodologies will not be provided here.

By one approach, this second radiation-treatment plan optimization process makes use of operating parameters for a specific radiation-delivery apparatus and/or a specific radiation-delivery method (that specifies, for example, a particular beam trajectory). Accordingly, this second radiation-treatment plan optimization process can account for and make use of the particular limitations and opportunities as tend to characterize a given radiation-delivery apparatus to thereby output a radiation-treatment plan that is specifically usable by a given corresponding radiation-delivery apparatus.

In some application settings there may be more than one radiation-delivery apparatus available for use. In such a case this second optimization stage 107 can readily accommodate running optimization plans for more than one specific radiation-delivery apparatus. So configured, the user can then select a particular radiation-delivery apparatus on the basis, at least in part, of which radiation-treatment plan seems best suited for the overall therapeutic aims for this particular patient.

Figure 2:
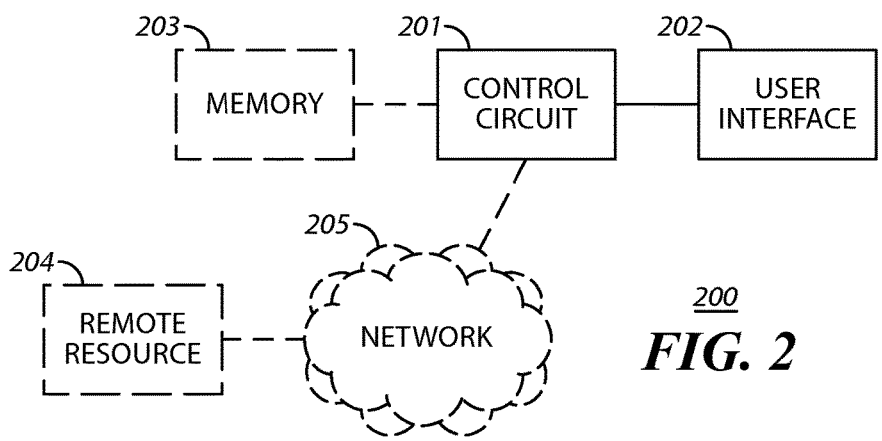
FIG. 2 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 2, an illustrative approach to such a platform will now be provided.

This apparatus 200 includes a control circuit 201 that operably couples to a user interface 202. Such a control circuit 201 can comprise a fixed-purpose hard-wired platform or can comprise a partially or wholly-programmable platform. All of these architectural options are well known and understood in the art and require no further description here. Particularly when the control circuit 201 comprises a partially or wholly-programmable platform, the control circuit 201 can also operably couple to an optional memory 203. This memory 203 can store information used when running the radiation-treatment plan optimization processes described herein. This memory 203 can also store the computer instructions that, when executed by the control circuit 201, cause the latter to carry out one or more of the steps, actions, and functions described herein as desired.

The user interface 202 can include, for example, one or more displays or other output interfaces to provide information to a user regarding optimization process results and/or presently-selected constraints. The user interface 202 can also include an input interface (such as a keyboard, touch screen, cursor-control device, or the like) to permit the user to select and/or modify the aforementioned user-selected constraints.

Information used by the control circuit 201 to carry out the described actions may be optionally gleaned, in whole or in part and as desired, from one or more remote resources 204 (such as corresponding information servers) via one or more intervening networks 205 such as the Internet.

Such an apparatus 200 may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

So configured, the overall time (and/or computational resources) required to formulate a fully-optimized radiation-treatment plan can be considerably reduced. Furthermore, a user's interaction time with such a process can be considerably reduced and thereby free that user to pursue other tasks. These teachings can be readily applied to a variety of optimization processes and hence can serve to greatly leverage the efficacy and continued value of such processes.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. As but one illustrative example in these regards, the second optimization stage 106 can make use of a plurality of different radiation-treatment plan optimization processes if desired. These different approaches can be employed serially if desired to further hone the results of a preceding process or can be employed independent of one another to permit comparisons between their plan results.

As another example in these regards, one or more properties of the dose distribution produced by during the first optimization stage can be used during the second optimization stage as objectives even though the user did not explicitly set those corresponding values as objectives. For example, the user might set a 30 Gy maximum dose limit for the spine. In this example the first optimization stage provides as an output that the thorax will receive 10 Gy and the user does not respond by defining any objective/constraint in these regards. This 10 Gy value may then be automatically used as a maximum limit for the thorax during the second optimization stage.

We claim:

1. A method to facilitate optimizing a radiation-treatment plan, the method comprising:
at a control circuit:
during a first optimization stage:
using a first radiation-treatment plan optimization process that concludes within a first period of time, that employs user-selected constraints that comprise non-machine-specific constraints, and that models at least one of a dose-distribution shape and a dose-distribution property to provide a first plan result, wherein the first plan result is non-specific with respect to a particular radiation-delivery apparatus and in particular is independent of any particular radiation-delivery method, such that the first plan result is independent of a radiation beam's specific trajectory, a speed at which a radiation source can be moved, an available number of collimators, any particular type of available collimator, a number of available collimator leaves, available collimator leaf shapes, a speed at which collimator leaves can be moved, and whether a corresponding patient support device is capable of movement;
providing an opportunity for a user to modify the user-selected constraints in view of the first plan result to thereby provide resultant vetted user-selected constraints;
during a second optimization stage:
using a second radiation-treatment plan optimization process that requires more than the first period of time to conclude and that employs the resultant vetted user-selected constraints to provide an optimized radiation-treatment plan, wherein the second radiation-treatment plan optimization process makes use of operating parameters for a specific radiation-delivery apparatus, wherein the operating parameters are specific and precise with respect to physical limitations of the specific radiation-delivery apparatus including movement speed limitations for a radiation source and speed limitations for changing aperture settings of a multi-leaf collimator, and wherein the second optimization stage yields the optimized radiation-treatment plan in less time than it would take the second optimization stage alone, in the absence of employing the resultant vetted user-selected constraints, to produce the optimized radiation-treatment plan.

2. The method of claim 1 wherein the user-selected constraints pertain, at least in part, to dosing requirements for a target and limitation-of-exposure requirements for non-targets.

3. The method of claim 1 wherein the second optimization stage offers reduced opportunities for dynamic user interaction as regards modification of the user-selected constraints as compared to the first optimization stage.

4. The method of claim 1 wherein the second radiation-treatment plan optimization process comprises a more precise optimization process than the first radiation-treatment plan optimization process.

5. The method of claim 4 wherein the second radiation-treatment plan optimization process comprises a higher-resolution version of the first radiation-treatment plan optimization process.

6. The method of claim 1 wherein the first radiation-treatment plan optimization process employs simpler models pertaining to a treatment target area as compared to the second radiation-treatment plan optimization process.

7. The method of claim 1 wherein the first radiation-treatment plan optimization process provides general plan results that are non-specific with respect to a particular radiation-delivery method.

\* \* \* \* \*